United States Patent
Schellenberg

(10) Patent No.: US 7,302,288 B1
(45) Date of Patent: Nov. 27, 2007

(54) TOOL POSITION INDICATOR

(75) Inventor: John D. Schellenberg, Cleveland Heights, OH (US)

(73) Assignees: Z-Kat, Inc., Ft. Lauderdale, FL (US); Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 08/756,257

(22) Filed: Nov. 25, 1996

(51) Int. Cl.
*A61B 5/00* (2006.01)
(52) U.S. Cl. .................. 600/427; 600/429; 606/130
(58) Field of Classification Search ............... 606/130; 600/434, 407, 420, 421, 410, 424, 179, 117, 600/109, 118, 427, 429; 434/262; 702/150–154, 702/159
See application file for complete search history.

(56) References Cited

U.S. PATENT DOCUMENTS

| | | | |
|---|---|---|---|
| 4,177,465 A * | 12/1979 | Lundvall et al. ............ 342/458 |
| 4,502,483 A | 3/1985 | Lacey |
| 4,604,992 A * | 8/1986 | Sato ........................... 600/179 |
| 4,654,701 A * | 3/1987 | Yabe ........................... 358/98 |
| 4,733,661 A * | 3/1988 | Palestrant ................... 606/108 |
| 4,836,778 A | 6/1989 | Baumrind et al. |
| 4,917,111 A | 4/1990 | Pennig et al. |
| 4,945,914 A | 8/1990 | Allen |
| 5,005,592 A * | 4/1991 | Cartmell ..................... 128/899 |
| 5,050,608 A | 9/1991 | Watanabe et al. |
| 5,143,208 A * | 9/1992 | Shostek et al. ............. 200/187 |
| 5,186,174 A | 2/1993 | Schlondorff et al. |
| 5,222,499 A | 6/1993 | Allen et al. |
| 5,230,338 A | 7/1993 | Allen et al. |
| 5,299,288 A * | 3/1994 | Glassman et al. ............ 395/80 |
| 5,309,913 A * | 5/1994 | Kormos et al. .......... 128/653.1 |
| 5,325,873 A * | 7/1994 | Hirschi et al. .............. 128/899 |
| 5,351,692 A * | 10/1994 | Dow et al. ............. 128/662.06 |
| 5,373,317 A * | 12/1994 | Salvati et al. ................. 348/65 |
| 5,383,454 A | 1/1995 | Bucholz |
| 5,389,101 A * | 2/1995 | Heilbrun et al. ............ 606/130 |
| 5,517,990 A | 5/1996 | Kalfas et al. |

(Continued)

FOREIGN PATENT DOCUMENTS

WO        9315648      *  8/1993   ................. 600/179

(Continued)

OTHER PUBLICATIONS

"A Frameless Stereotaxic Operating Microscope for Neurosurgery", Friets, et al.; IEEE Transactions on Biomedical Engineering; vol. 36, No. 6, Jun. 1989, pp. 608-617.

*Primary Examiner*—Ruth S. Smith
(74) *Attorney, Agent, or Firm*—Fay Sharpe LLP

(57) ABSTRACT

A tool for use with a surgical navigation system includes a plurality of LEDs mounted to the distal end of the tool. The LED's provide an indication of the direction in which the tool must be moved to reach a desired position. Four LED's mounted along perpendicular axes are provided. Modes for indicating the desired location, orientation, rotation, and depth are provided. A mode indicator may also be provided. The tool is designed for use with a surgical navigation system which includes an infrared localizer and computer system. The indicators assist the surgeon in positioning the surgical tool in relation to the patient. Indicators other than LEDs may be used; the indicators may also be mounted in alternate locations in the operating room environment.

18 Claims, 5 Drawing Sheets

U.S. PATENT DOCUMENTS

| | | | |
|---|---|---|---|
| 5,588,430 A | * 12/1996 | Bova et al. | 128/653.1 |
| 5,622,170 A | * 4/1997 | Schulz | 128/653.1 |
| 5,638,819 A | * 6/1997 | Manwaring et al. | 600/424 |
| 5,662,111 A | * 9/1997 | Cosman | 128/653.1 |
| 5,682,890 A | * 11/1997 | Kormos et al. | 128/653.2 |
| 5,711,299 A | * 1/1998 | Manwaring et al. | 600/424 |
| 5,772,594 A | * 6/1998 | Barrick | 600/407 |
| 5,776,050 A | * 7/1998 | Chen et al. | 600/117 |
| 5,782,842 A | * 7/1998 | Kloess et al. | 606/130 |
| 5,868,675 A | * 2/1999 | Henrion et al. | 600/424 |
| 5,879,289 A | * 3/1999 | Yarush et al. | 600/179 |
| 5,891,034 A | * 4/1999 | Bucholz | 600/426 |

FOREIGN PATENT DOCUMENTS

WO      WO93/15648    *   8/1993

* cited by examiner

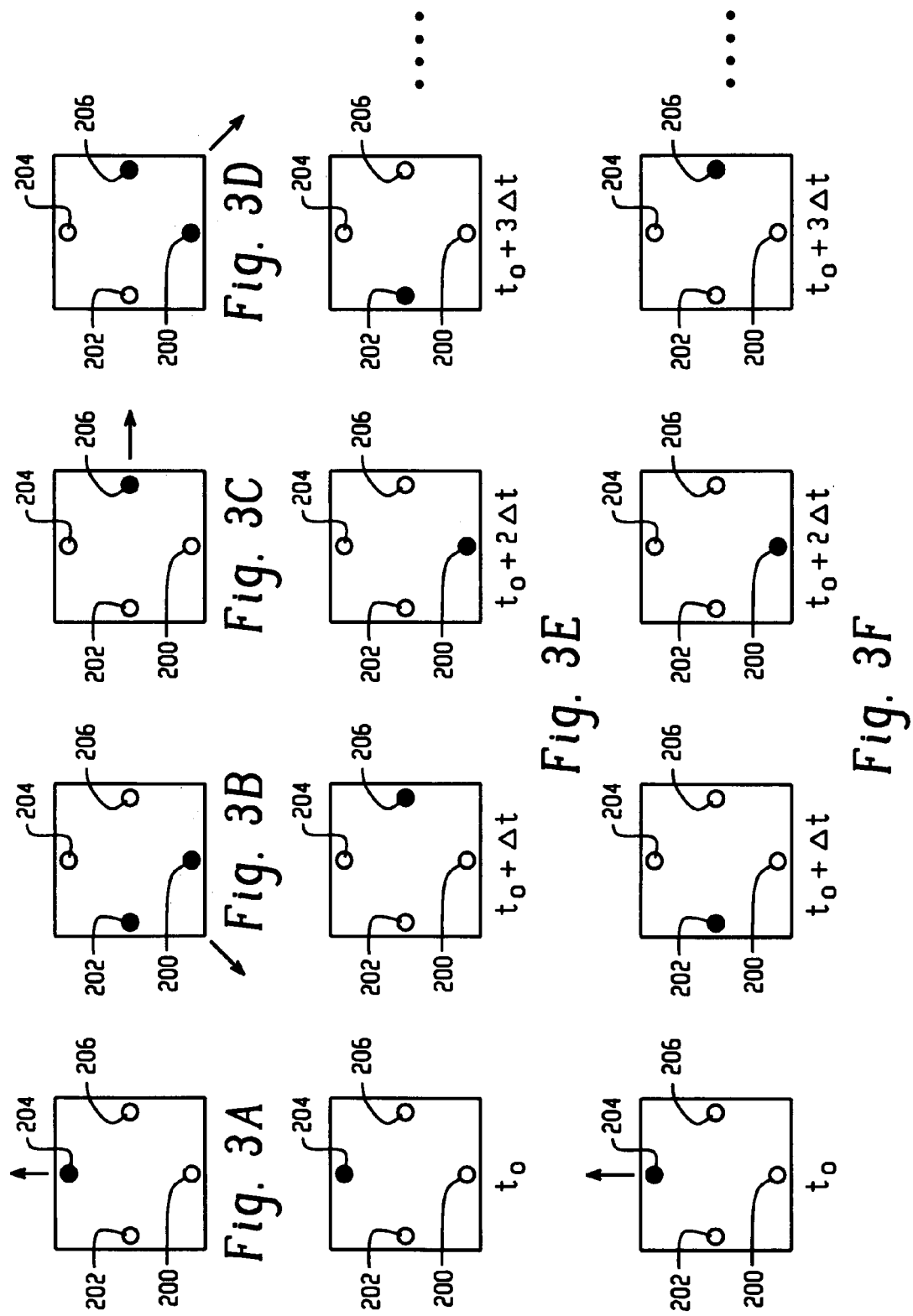

TOOL POSITION INDICATOR

BACKGROUND

The present invention relates to the medical diagnostic and surgical arts. It finds particular application in conjunction with neurosurgery and will be described with particular reference thereto. However, it is to be appreciated that the invention will also find application in conjunction with various medical procedures, including neurobiopsy, CT-table needle body biopsy, breast biopsy, endoscopic procedures, orthopedic surgery, and the like.

Three-dimensional diagnostic images of the brain, spinal cord, and other body portions are produced by diagnostic imaging equipment such as CT scanners, magnetic resonance imagers, and the like. These imaging modalities often provide structural detail with a resolution of a millimeter or better.

Image guided surgery systems have been developed to utilize this data to assist the surgeon in presurgical planning and in accurately locating a region of interest within the body of a patient. In the operating theater, these systems are used to display position and orientation of a surgical tool in its correct location with respect to the images of the patient. One example of an image guided surgery system is U.S. Pat. No. 5,517,990, Stereotaxy Wand and Tool Guide, to Kalfas et al. issued May 21, 1996, incorporated by reference herein.

Three and sometimes four views of image data are displayed on a monitor visible to the surgeon. These views typically include axial, sagittal, and coronal views of the patient. A fourth oblique view is sometimes displayed, presenting image data in a plane orthogonal to the tip of the probe. The location of the tip of the tool and the tool's trajectory, together with the desired location and trajectory, are displayed on one or more of these images. The algebraic distance between the tip of the tool and a desired position may also be displayed numerically on the monitor. The distance may also be calculated along an axis orthogonal or parallel to the plane of one or more of the views.

Although image guided surgery systems are more accurate and provide the surgeon with more information compared to previous techniques, it is sometimes difficult to visualize, with reference to image data displayed on the monitor, the manipulation required to place the surgical tool in the desired position and orientation. As will be appreciated, the surgeon is required to visualize the position of the tool with respect to the image data and then relate that information to a required motion of the tool in relation to the patient. This task is complicated by the three dimensional nature of the required manipulation, the two dimensional nature of the images, and the often disparate positions of the monitor and the patient.

Current systems also require that the surgeon view the monitor to determine the position of the tool. The surgeon is thus forced to divert his or her attention from the tool and the patient, thereby complicating the positioning process. Accordingly, it would be desirable to provide the surgeon with a readily understandable indication of the proper tool position and orientation without requiring the surgeon to divert his or her attention to a remote monitor or display.

The present invention provides a new and improved method and apparatus which addresses the above-referenced matters, and others.

SUMMARY

According to a first aspect of the invention, an apparatus for guiding the movement of a surgical tool comprises means for indicating the difference between the actual and desired position of the tool. According to another aspect of the invention, the tool has a tool reference frame and the difference is indicated with respect to the tool reference frame. According to a further aspect, the means for indicating is mounted to the tool. The means for indicating may further include at least one light emitting diode which indicates a direction and orientation in which the tool should be moved to reach the desired position. According to other aspects of the invention, the means for indicating may be a light emitting diode or an LCD display.

According to yet another aspect of the invention, the apparatus further comprises means for defining a desired position of the tool based on an image of the anatomy of a patient, means for determining the actual position of the tool, and means for determining the difference between the actual and desired positions. The means for determining the position may include, for example, an infrared localizer, a laser locating device, an ultrasonic localizer, an articulated arm, or the like.

According to yet other aspects of the invention, the actual and desired positions of the tool are at least one of a desired location, trajectory, depth, and rotation of the tool. The tool, which may be a tool guide, may also include a position indicator and a mode indicator. The indicating means may also include a plurality of indicators mounted in a plane substantially orthogonal to the pointing axis of the tool. The indicating means may also provide an audible indication.

According to a further aspect of the invention, an apparatus for guiding a surgical tool in relation to the anatomy of a patient comprises a surgical tool and at least one position indicator. The indicator provides an indication of one or both of the direction or distance in which the tool should be moved to reach a desired position. The desired position may be at least one of a desired location, orientation, depth, and rotation. The tool may include first and second position indicators arranged along a first line and second and third indicators arranged along a second line. The first and second lines are perpendicular.

According to yet another aspect of the invention, an apparatus for guiding the movement of a surgical tool with respect to the anatomy of a patient includes a surgical tool, means for defining a desired position of the tool based on an image of the anatomy, means for determining the actual position of the tool; means for determining the difference between the actual and desired positions, and at least one indicator mounted to the tool, the indicator providing an indication of the difference between the actual and desired positions.

According to still another aspect of the invention, a surgical tool comprises a plurality of infrared emitters and at least one position indicator.

According to still other aspects of the invention, a method for guiding the movement of a surgical tool is provided. A desired position is defined with respect to an image of a patient's anatomy. The actual position of a surgical tool is determined with respect to the patient, and reference frames associated with the image and the patient are correlated. The direction the tool must be moved to reach the desired position is determined, and the direction in which the tool must be moved to reach the desired position is indicated. According to other aspects of the invention, the direction is indicated in relation to the tool reference frame. The distance the tool must be moved may also be determined and indicated. The distance and direction may be indicated by varying the blink rate or color of an indicator.

According to still further aspects of the present invention, the patient is supported by a patient support and the step of indicating utilizes an indicator mounted in fixed relation to the support. The method may further comprise the steps of establishing a threshold, determining the difference between the actual and desired positions, and indicating that the tool must be moved only if the distance is greater than the threshold. According to another aspect, a mode is selected and indicated. Based on the mode, the direction in which the tool must be moved to reach one of a desired location and orientation is indicated.

Other aspects, advantages, and features of the invention will be apparent from the following description of the preferred embodiment and the accompanying drawings.

DESCRIPTION OF THE DRAWINGS

The invention may take form in various components and arrangement of components, and in various steps and arrangements of steps. The drawings are only for purposes of illustrating a preferred embodiment and are not to be construed as limiting the invention.

FIGS. 3A-3F depict signals provided by the position indicators.

DESCRIPTION

Figure 1A:
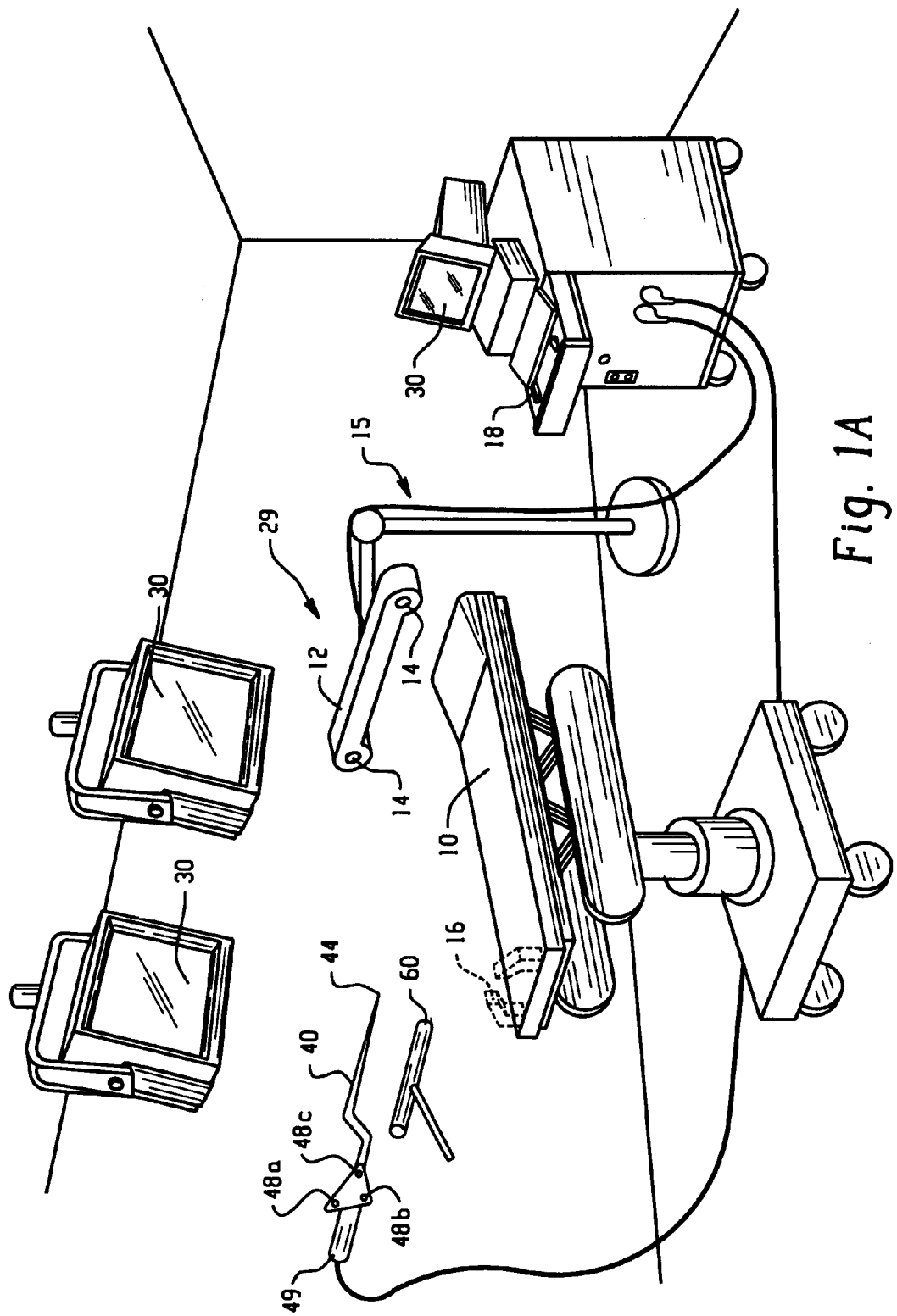
FIG. 1A is a perspective view of an operating room in which the present invention is deployed.

A patient reference frame is defined using three or more reference points fixed in relation to the anatomy of the patient. According to one method, at least three fiducial markers visible to the imaging device are affixed to the skin prior to imaging. The fiducials are markers or small beads that contain material visible using a desired imaging technique. A small dot or tattoo is made on the patient's skin and a fiducial is glued to each dot. This enables the position of the fiducial to be denoted even if the fiducials are removed in the interval between the collection of the image data and the surgical procedure.

The fiducials may also be affixed to the patient using attachment means such as screws. Thus, for example, three or more fiducial markers may be affixed to the skull of the patient to define a reference frame with respect to the patient's head. Fiducial markers may of course be affixed to other portions of the anatomy to define a reference frame with respect thereto.

According to another technique, three or more anatomical reference points more are used. In spinal surgery, for example, reference points may be defined with respect to the spinous and transverse processes. In cranial surgery, reference points may be defined with respect to the nasion and other readily identifiable reference points. Of course, reference points may also be defined with respect to other portions of the anatomy.

Conventional stereotactic locating frames may also be used to define the patient reference frame.

An image of the patient is obtained using magnetic resonance, computed tomography or other technique which produces a volumetric image of the patient's anatomy. A three dimensional image is produced and contains video value for each voxel in a three dimensional grid, preferably a 256×256×256 grid. When each image value represents a one millimeter cube, the image data represents about a 25.6 centimeter cube through the patient. The image data is characterized by its own image frame of reference. Based on the location of the three or more reference points within the image data, the image and patient reference frames can be correlated or registered. Stated another way, the position of a feature of interest within the image can be determined with respect to its position with the patient.

This information can be used to assist the physician with presurgical planning and to provide information relating to the position and orientation of the anatomy and surgical instrument during a surgical procedure. For example, the surgeon may wish to define a target 27c, entry point 27a, other desired location of a surgical tool or probe with respect to a feature visible in the image. One example of such a target is a lesion. Similarly, the surgeon may wish to define a desired trajectory 27b to reach the target. The surgeon may also wish to define a desired rotational orientation 27d of the surgical tool.

The applicable locations, trajectory, or orientation are entered by the surgeon using operator console 18 in conjunction with the monitor 30. For example, the surgeon may use a trackball or mouse (not shown) in connection with a cursor displayed on the monitor 30 to designate a target and entry point with respect to one or more displayed images. Once these points have been defined, a computer system can calculate and display the desired trajectory.

With reference to FIG. 1A, the patient is received on an operating table or other subject support 10 and appropriately positioned within the operating room. A securing means such as a head clamp 16 securely positions a portion of the subject under consideration. A locating device 29 such as an infrared localizer determines the location 159a and orientation 159b of at least one surgical tool.

In the preferred embodiment, the locating device is an infrared localizer such as the Polaris™ localizer system supplied by Northern Digital, Inc. of Waterloo, Ontario, Canada. The localizer system includes two spaced apart infrared cameras 14 mounted on a sensor head 12. The sensor head 12 is in turn mounted in a fixed position within the operating room, for example on a stand 15 resting on the floor. The cameras 14 may be mounted in another known position in the operating room environment, such as to the ceiling or wall or to the subject support 10. Of course, other locating devices, such a ultrasonic, optical, or electromagnetic localizers, may be used. The surgical tool may also be mounted to an articulated arm, the arm functioning as the locating device.

Figure 1B:
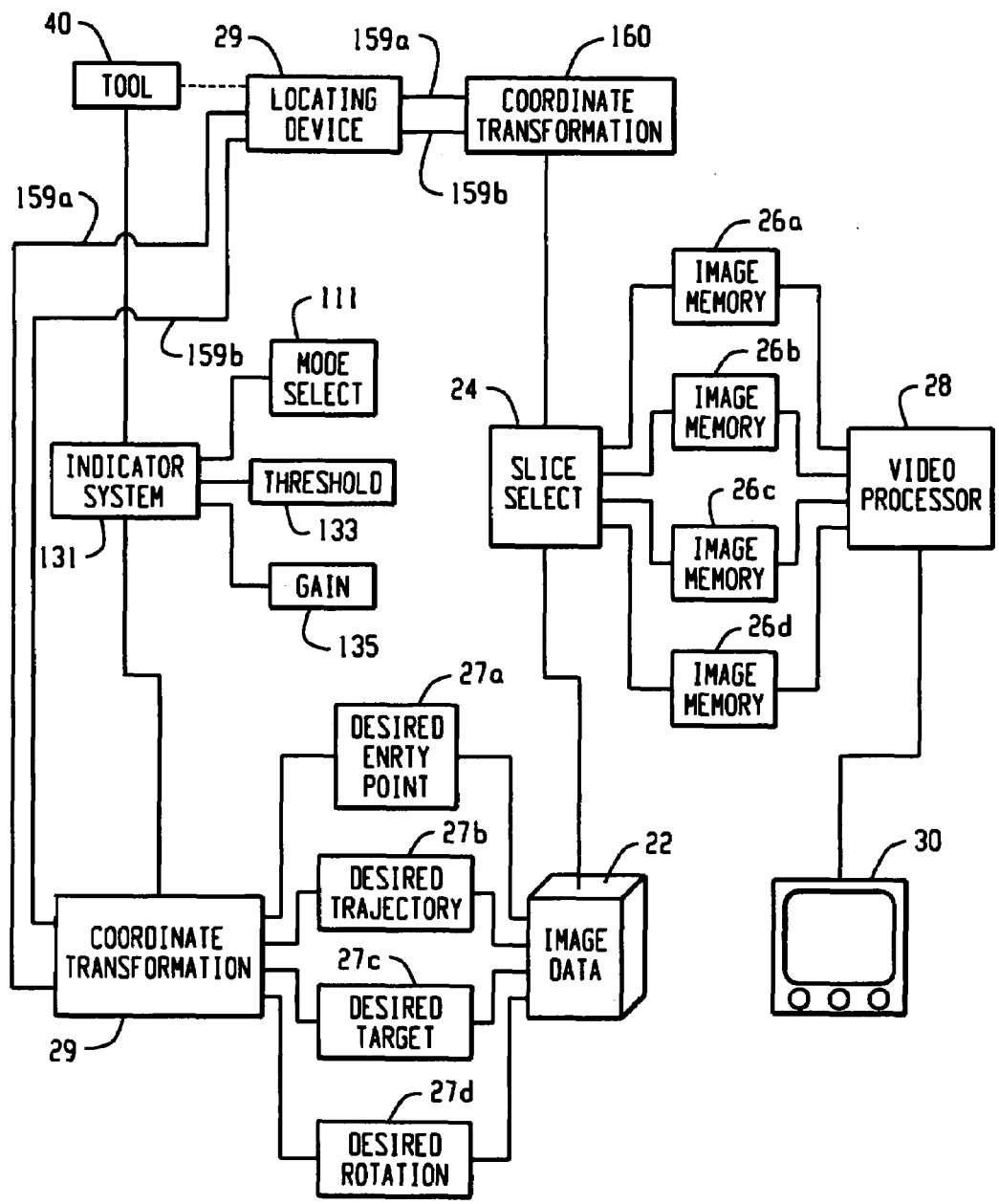
FIG. 1B is a block diagram of a system according to the present invention.

With continuing reference to FIG. 1A and further reference to FIG. 1B, an operator console 18 houses a computer system. Alternately, the computer system can be remotely located and connected with the control console 18 by cabling. The computer system includes a data memory 22 which contains data indicative of a three-dimensional image of the patient. Because the data can be visualized as a three-dimensional rectangular grid, selectable orthogonal and other oblique planes of the data can be readily withdrawn from the memory using conventional technology.

The plane or slice selector 24 selects axial, sagittal, coronal, and oblique planes through a selectable point of the patient from the image data 22 for display on the monitor 30.

The pixel values which lie on the selected planes are copied into corresponding image memories 26a, 26b, 26c, 26d. A video processor 28 converts the two-dimensional digital image representations from one or more of image memories 26 into appropriate signals for display on video monitors 30 or other appropriate image displays.

Figure 2:
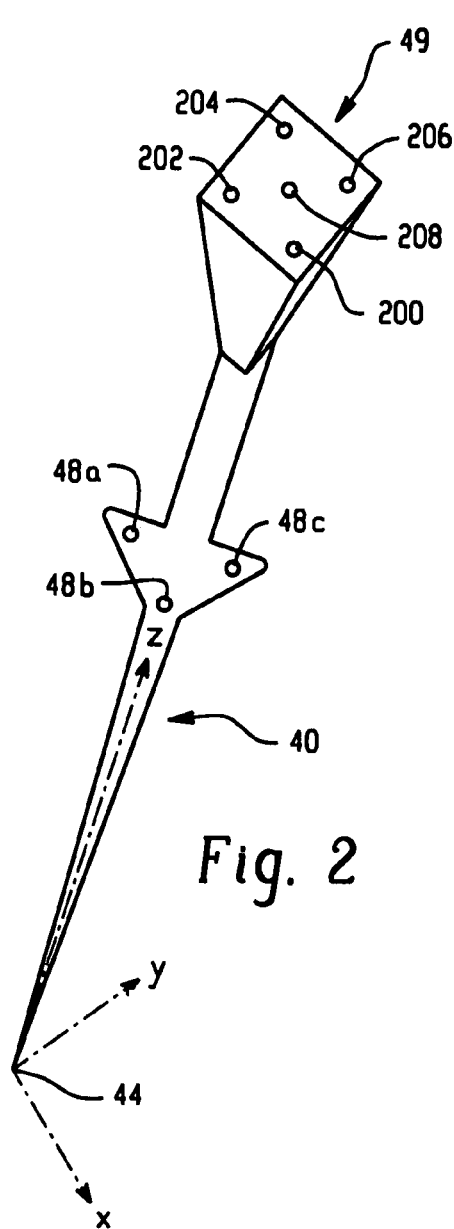
FIG. 2 is a perspective view of a surgical tool.

With reference to FIGS. 1A and 2, the surgical wand or tool 40 is characterized by a tool reference frame. For example, the tool reference frame may be defined such that the origin is at the tip 44 of the tool 40 and having an axis substantially collinear with the pointing axis of the tool 40. The tool 40 includes at least three infrared emitters 48a, 48b, 48c having a known relationship to the tool reference frame. Additional emitters may be used to provide a redundant indication in case the line of sight between of the emitters and the cameras is blocked or to permit more accurate determination of the position of the tool. Based on the signals detected by the cameras 14, the location and orientation of the tool 40 and hence the tool reference frame with respect to the cameras 14 and hence the operating room reference frame are determined. The position of the patient may also be determined using three or more infrared emitters mounted to the securing means or clamped in a fixed relation to the patient.

The patient, image, tool, and operating room reference frames are correlated or registered by touching the tip 44 of the surgical tool 40 to the at least three reference points defined in relation to the patient and determining the location 159a and orientation 159b of the tool 40 at each point.

Based on this information, the transforms between patient, image, tool, and operating room reference frames can readily be calculated. As is well known in the art, a transform is accomplished by determining an offset $x_{offset}$, $y_{offset}$, $z_{offset}$, between the reference frames to be transformed. These values of $x_{offset}$, $y_{offset}$, $z_{offset}$ are added to or subtracted from the coordinates of one of the reference frames as required to translate between the two. The coordinate systems are then rotated relative to each other about their origins by angles $\alpha$, $\beta$, $\gamma$ so that their respective x, y, and z axes coincide.

Coordinate transform 160 transforms or matches the patient and image reference frames. The location and orientation of the tool are connected though the transform 160 with the slice select 24 and the video processor 28 to display the location of the tool tip 44 and the trajectory of the tool 40 superimposed on one or more selected images of the patient. The display is updated approximately four times per second to provide a real time indication of the tool position. The desired entry point, trajectory, target, and rotation may be similarly displayed with respect to the appropriate images. The difference between the actual and desired position of the tool is readily calculated. The direction and distance which the tool must be moved to reach a desired position is also readily calculated.

The tool 40 also includes a position indicator system 131 which includes one or more indicators such as a human readable display or visible LED's 200, 202, 204, 206, 208 mounted in a known relation to the tool reference frame. The indicators are preferably mounted at the distal end 49 of the tool so as to be readily visible to the surgeon and in a plane generally orthogonal to the pointing axis of the tool 40.

The mode indicator 208, which indicates the mode of the system, is preferably a multicolor LED such as a red/green LED. The position indicators 200, 202, 204, 206 are used to indicate a direction in which the tool should be moved to reach a desired position. Stated another way, the position indicators 200, 202, 204, 206 indicate the difference between the actual and desired position of the tool. Two position indicators 200, 204 are mounted along a first line; two other position indicators 202, 206 are mounted along a second line perpendicular to the first. The mode indicator 208 is mounted so as to readily distinguished from the position indicators 200, 202, 204, 206, for example in their approximate center.

Coordinate transform 160 transforms or matches the image and tool reference frames. The location and orientation of the tool are connected through the transform 160 with the position indicator system to indicate the direction in which the tool must be moved to reach a desired position. By determining the location and orientation of the tool, the location and orientation of the indicators such as LEDs 200, 202, 204, and 206 are also determined. Stated another way, the location and orientation of the indicators are determined. Knowing this information, the appropriate LEDs are illuminated to indicate the direction in which the tool should be moved.

The indicator system has at least location and orientation modes. The modes may be selected by the surgeon using a mode select 111 such as a foot switch, a switch located on the tool, or through the operator console 18. The location mode is indicated, for example, by illuminating the mode indicator 208 to be green in color. In location mode, the position indicators indicate the difference between an actual and desired tip location. Stated another way, the position indicators indicate the direction in which the tip 44 should be moved to reach the desired location. This information is preferably provided with respect to the tool's x-y plane, i.e., in a plane orthogonal to the pointing axis of the tool.

The orientation mode is indicated by illuminating the mode indicator 208 to be red in color. In orientation mode, the position indicators 200, 202, 204, 206 indicate the difference between an actual and desired tool orientation. Stated another way, the position indicators indicate the angular direction in which the tool 40 should be moved to reach a desired orientation.

Additional modes are also contemplated. A depth mode is used to indicate the difference between an actual and desired depth. Stated another way, the position indicators indicate the direction which the tool tip 44 should be moved along its pointing or z-axis to reach a desired location. Similarly, a rotate mode is used to indicate the difference between an actual and desired tool rotation. Stated another way, the position indicators indicate the direction the direction in which the tool should be rotated about its z axis to reach a desired rotational orientation. These modes are indicated by causing the mode indicator 208 to blink. For example, the depth mode may be indicated by causing the mode indictor 208 to blink green in color. The rotate mode may be indicated by causing the mode indicator 208 to blink red in color.

Examples of the signals provided by the position indicators 200, 202, 204, 206 in location mode are shown in FIGS. 3A and 3B. FIG. 3A shows position indicator 204 illuminated while positions indicators 202, 206, and 200 are dark. This indicates that the tip 44 of the tool should be translated in the direction of indicator 204 to reach the desired location. FIG. 3B shows position indicators 200, 202 illuminated while position indicators 204, 206 are dark. This indicates that the tip of the tool should be moved in the direction of the illuminated position indicators 200, 206 to reach the desired location. When the tool reaches the desired location, the position indicators are no longer illuminated.

Examples of the signals provided by the position indicators 200, 202, 204, 206 in orientation mode are shown in FIGS. 3C and 3D. FIG. 3C shows position indicator 206 illuminated while position indicators 200, 202, 204 are dark. This indicates that the angular position or orientation of the tool should be changed by moving the distal end of the tool in the direction of indicator 206 to reach the desired orientation. FIG. 3D shows position indicators 200, 206 as illuminated while position indicators 202, 204 are dark. This indicates that the angular position or orientation of the tool should be changed by moving the distal end 49 of the tool in the direction of the illuminated position indicators 200, 206. Of course, the desired angular position could also be reached by moving the tool tip 44 in the opposite direction. When the tool reaches the desired orientation, the position indicators are no longer illuminated.

Examples of the signals provided by the position indicators 200, 202, 204, 206 in the depth mode are shown in FIGS. 3E and 3F. FIG. 3E shows the position indicators being illuminated sequentially in a clockwise direction at multiples of time interval $\Delta t$. This indicates that the tool should be moved in the -z direction to reach the desired location. FIG. 3F shows the position indicators being illuminated sequentially in a counterclockwise direction, again at multiples of time interval $\Delta t$. This indicates that the tool should be moved in the z direction to reach the desired location. When the tool reaches the desired location, the position indicators are no longer illuminated.

Examples of the signals provided by the position indicators 200, 202, 204, 206 in the rotate mode are also shown in FIGS. 3E and 3F. FIG. 3E shows the position indicators being illuminated sequentially in a clockwise direction at multiples of time interval $\Delta t$. This indicates that the tool should be rotated about the z-axis in the direction of rotation, i.e. clockwise when viewed from the distal end. FIG. 3F shows the position indicators being illuminated sequentially in a counterclockwise direction, again at multiples of time interval $\Delta t$. This indicates that the tool should be rotated about the z axis in the direction of rotation, i.e. counterclockwise when viewed from the distal end. When the tool reaches the desired orientation, the position indicators are no longer illuminated.

Figure 4A:
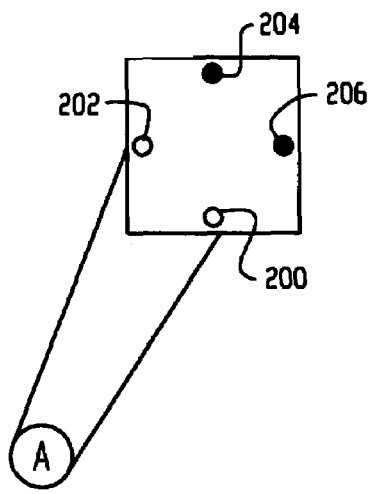
FIGS. 4A-4C are perspective views of a surgical tool which demonstrate rotational invariance.
Figure 4B:
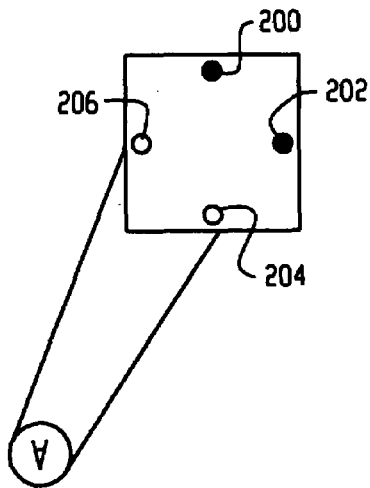
Figure 4C:
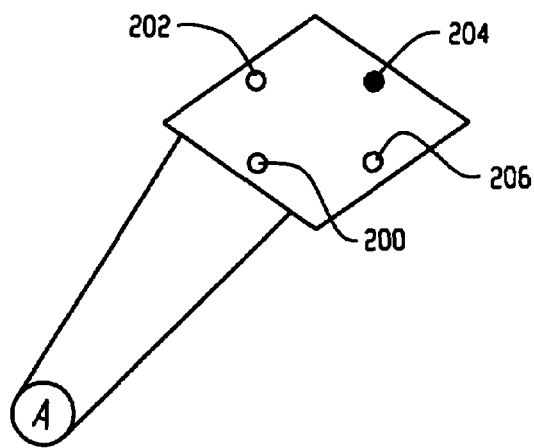

With reference to FIG. 4, the signals provided by the position indicators are rotationally invariant Stated another way, the position indicators provide positional information with respect to the tool reference frame such that positional information is correctly indicated irrespective of the orientation of the tool and hence the position indicators. FIG. 4A depicts a tool in location mode with position indicators 204, 206 illuminated to indicate the direction in which the tool tip should be moved. The upright letter "A" indicates the rotational orientation of the tool about its z axis. As indicated by the inverted letter "A" at the position of the tool tip 44, FIG. 4B depicts the tool with the tip 44 in the same position but with the tool rotated 180° about its z axis. Position indicators 200, 202 are now illuminated and indicate that the direction of the translation of the tool tip remains unchanged. As the tool is rotated between the rotational orientations shown in FIGS. 4A and 4B, the tool will reach an orientation, depicted in FIG. 4C, where only indicator 204 is illuminated. This indicates that the tip of the tool should be moved in the direction of the illuminated indicator 204. In the illustrated example, it should also be noted that there are three other rotational orientations where only a single indicator will be illuminated. As will be appreciated, rotational invariance is equally applicable to the other system modes.

Figure 2A:
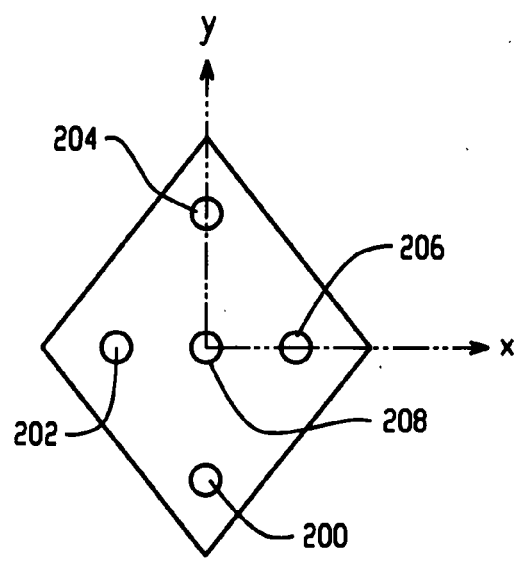
FIGS. 2A-2D depict different embodiments of position and mode indicators.
Figure 2B:
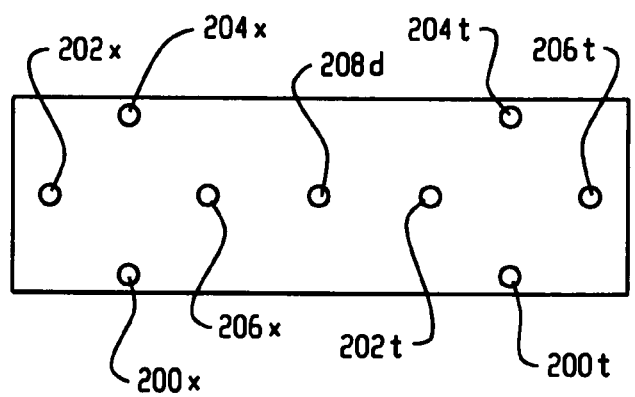

More than one set of position indicators 200, 202, 204, 206 may also be provided. For example, a set of position indicators may be provided for each of the system modes. FIG. 2B depicts such an implementation for a system having location, orientation, and depth modes. Position indicators 200$x$, 202$x$, 204$x$, 206$x$ indicate the necessary movement of the tool tip 44 to reach the desired location. Indicators 200$t$, 202$t$, 204$t$, 206$t$ indicate the necessary angular movement of the tool to reach the desired orientation.

Indicator 208$d$ is a two color LED used to provide a depth indication analogous to that described above in FIGS. 3E and 3F. Illuminating the depth indicator 208$d$ to be red in color indicates that the tool tip 44 should be moved in the tool z direction. Illuminating the depth indicator to be green in color indicates that the tool tip 44 should be moved in the tool -z direction.

A mode indicator is of course not required where a set of position indicators is provided for each of the system modes. The system mode may also be selected and displayed by a switch mounted on the tool or other convenient location. Where required, the mode of the indicator system may be displayed in alternate ways. For example, a plurality of mode indicators may be used. For example, a separate mode indicator may be provided for each of the system modes, with the corresponding indicator illuminated to indicate the appropriate mode. The system mode may also be displayed using indicators remote from the tool yet readily visible by the surgeon, for example affixed to the patient support 10, the head clamp 16, or other structure. The mode may also be displayed on one or more of the monitors 30.

In addition to indicating the direction in which the tool should be moved, the position indicators 200, 202, 204, 206 provide a relative indication of the magnitude of the required motion. For example, a relatively large translation or angular movement is indicated by causing the relevant indicator to blink relatively quickly; a small translation or angular movement is indicated by causing the indicator to blink relatively slowly. Where the magnitude of the motion is indicated by sequentially illuminating the indicators as shown in FIGS. 3E-3H, the magnitude is indicated by varying the rate at which the indicators are sequentially illuminated. Stated another way, time interval $\Delta t$ is varied. The magnitude of the required movement may also be indicated by varying the brightness of the indicator. A relatively large movement is indicated by causing the indicator to be brightly illuminated; a small movement is indicated by causing the indicator to be dimly illuminated. Multicolor indicators such as red/green LED's can also be used.

Threshold 133 and gain 135 settings are also established for each of the modes. The threshold setting 133 defines a minimum difference between an actual and desired position, orientation, or rotation, as the case may be, which will cause the position indicator system to indicate that movement of the tool is required. The gain setting 135 defines the relationship between the indicator blink rate or other displacement indication and the difference between the actual and desired location, depth, orientation, or rotation. The threshold 133 and gain 135 settings are preset within the computer and may be adjusted by the surgeon using the operator console 18 depending on the needs of a particular surgical operation.

The position indicator system may be used in connection with any surgical tool where it is necessary to guide the position or trajectory of the tool with respect to a patient. For example, the system may be used in connection with a wand or probe, a drill or forceps, or a tool guide. With reference to FIG. 1A, a tool guide 60 ordinarily includes a guide means such as a bore for defining the trajectory of a surgical tool. Although the tool guide in FIG. 1A is depicted as being hand held, it will be appreciated that the tool guide may also be mounted to a suitable structure within the operating room such as the patient support 10, the head clamp 16, the body of the patient, or the like. Similarly, the tool guide may take one of several forms, such as a guide block or the like. Inasmuch as the axis of the guide means with respect to the tool guide is known, the trajectory or orientation of a tool inserted in the bore is known. Similarly, the location of a point having a known location along the guide axis can be determined. For the purposes of adjusting the tool guide, such a point is used to define location of the tip of a tool which will be inserted therein.

In such an embodiment, the tool guide includes three or more emitters 48 and indicators 200, 202, 204, 206, 208. The emitters and indicators function as described above, and the surgeon uses the indicators to position the tool guide so that one or more of a desired location, orientation, depth, and rotation are achieved. Once the tool guide has been positioned, the tool guide may be secured in place, and the tool inserted as desired.

According to a second embodiment, only the tool used in connection with the tool guide includes the emitters and indicators. In such an embodiment, the surgeon uses the indicators mounted on the tool to adjust its position. Of course, both the tool and the tool guide may include emitters and indicators. Similarly, the tool guide may contain emitters while the tool contains indicators, or vice versa. Hence, the position indicator system can be used to facilitate the positioning of a tool guide, either with or without a tool inserted therein, depending on the needs of a particular application.

In operation, reference points are defined with respect to the patient's anatomy and images of the patient are obtained. Depending on the requirements of a particular surgical operation, the surgeon designates a target location, entry point, trajectory, and/or rotation with respect to the image data using operator console 18. In cranial surgery, for example, the surgeon may designate the target as a point within a lesion and define and entry point on the exterior of the patient's anatomy. The surgeon may also elect to adjust the gain and threshold of the system indicators. After the patient is moved to the operating room, the patient and image reference frames are registered. The transforms between the patient, image, and tool reference frames are then calculated by the computer.

The system is first placed in location mode. The tip of the tool is then placed on an estimated entry point. Position indicators 200, 202, 204, 206 indicate the direction in which the probe tip 44 must be moved to reach the entry point. With reference to FIG. 2A, indicators 204, 206 may be illuminated to indicate that the tip 44 should be translated generally in the direction of the illuminated indicators, with the blink rate providing an indication of the magnitude and direction of the required motion. For example, position indicator 204 may be blinking relatively slowly while position indicator 206 is blinking relatively rapidly. This would indicate that the tip 44 should be translated predominantly in the direction of the position indicator 206. The tip 44 is translated until the position indicators are no longer illuminated. Proper positioning can be verified with reference to the position of the tool as displayed with respect to the image data on one of the monitors 30.

As described above, an advantage of the system is its rotational invariance. This property can be advantageously used to position the tool. The tool 40 is rotated about its z-axis until only one of the position indicators 200, 202, 204, 206 is illuminated. The tool tip 44 is then translated in the direction of the illuminated position indicator. The indicator blink rate provides an indication of the required distance.

The system can then also be used to place the tool 40 in the desired trajectory or orientation. The system is placed in trajectory guidance mode, and the illumination of the position indicators 200, 202, 204, 206 is observed. The angular position of the tool is adjusted as indicated by the position indicators. As will be appreciated, the rotational invariance of the indicator system can be used by rotating the tool 40 about its z-axis until only one position indicator is illuminated. The distal end of the tool is then moved in the direction of the illuminated indicator.

To determine the depth needed to reach a target, the system is placed in depth mode. Position indicators 200, 202, 204, 206 are illuminated sequentially in the clockwise direction to indicate that the tip of the probe should be moved in the -z direction and sequentially in the counterclockwise direction to indicate movement in the z direction, with the rate at which the indicators are sequentially illuminated providing an indication of the amount of movement needed. In an embodiment utilizing a multicolor depth indicator 208*d* as shown in FIG. 2B, the color of the indicator indicates the direction of motion.

The indicators 200, 202, 204, 206, 208 or other display may advantageously be mounted remote from the surgical tool 40 but convenient to the surgeon's line of sight. Thus, the indicators may be mounted in a known position on the patient support 10, the patient securing means such as head clamp 16, to a separate stand, or the like. Because the position and orientation of the indicators and hence the indicator reference frame is known in relation to the patient reference frame, the appropriate indicators can be illuminated to indicate the direction in which the tool should be moved, taking into account the relative orientations of the indicator and patient. Stated another way, positional information is provided with respect to the indicator reference frame.

The relative positions of the patient and the indicators may change during the course of a surgical procedure. For example, the position of the patient may be changed for the convenience of the surgeon or due to physiological motion such as respiration. Similarly, the surgeon may wish to move the indicators, for example to a more convenient location. By determining the relative positions of the patient and display, the appropriate indicators may be illuminated to account for changes in the relative positions.

This principle may be illustrated with reference to FIG. 4, it being understood in the present context that the display is mounted separately from the tool. Again, the signals provided by the position indicators are rotationally invariant. In this context, FIG. 4A depicts the display in location mode with position indicators 204, 206 illuminated to indicate the direction in which the tool should be moved. The upright letter "A" indicates the rotational orientation of the display with respect to the patient. As indicated by the inverted letter "A," FIG. 4B depicts the relative positions of the patient and display rotated by 180 degrees. Position indicators 200, 202 are now illuminated and indicate that the direction of the translation of the tool tip remains unchanged.

As will be appreciated, position of the indicators and hence the indicator reference frame may be determined by touching the tool tip 44 to three reference points defined in relation to the indicators. Similarly, the position of the indicators may be determined by placing three or more emitters on the indicator assembly such that the position of the indicators may be determined by the locating device.

In some applications, it may be also be desirable to locate certain of the indicators on the surgical tool while others are remotely located. Thus, a depth indicator may be located on the tool 40 while indicators for tip and trajectory guidance may be mounted to the patient support, or vice versa.

Figure 2C:
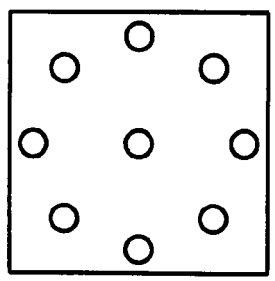
Figure 2D:
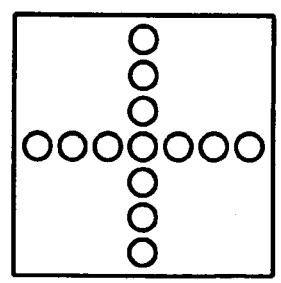

The indicators may also be arranged in any number of configurations. With reference to FIG. 2C, additional indicators may be mounted circumferentially to provide a more precise indication of the direction of motion. With reference to FIG. 2D, additional detectors may also be mounted radially, with the illumination of indicators in the radial direction indicating the distance the tool 40 should be moved.

It will also be appreciated that the position indicators may be illuminated in a manner which is the opposite of that described above. Thus, an illuminated indicator may indicate that movement in a particular direction is not necessary; the tool is moved in the direction of a darkened indicator until it is illuminated.

The system may also be used to provide an indication that an indicator is inoperative. Thus, the system may cause the indicators to blink periodically. Similarly, the surgeon may enter an indicator test command using a foot pedal, switch, the operator console 18 or the like. This command illuminates all of the indicators so that an inoperative indicator is readily identified.

Indicators other than LEDs may also be used. For example, graphic or alphanumeric displays such as LCD, LED, or elecroluminescent displays may be used. Use of a display having graphics capabilities facilitates the use of graphic symbols such as pointers to indicate a direction of motion. A display having alphanumeric capability allows the amount of required motion to be displayed numerically.

The system may also be used to indicate that the tool has moved from a previously established position. For example, the surgeon may place the tool at the entry point using the location mode and then switch to the orientation mode to position the tool in the desired trajectory. An alarm is used to inform the surgeon if the location of the tool tip 44 is inadvertently changed. This alarm may be provided by an audible indication or a visible indication on the monitor 30 or one of the indicators.

Both the direction and magnitude of the required motion can be indicated audibly using a loudspeaker, headphones, or the like. For example, means for synthesizing speech are well known in the art. Based on the difference between the actual and desired positions, and indication of one or both of the direction and magnitude of the required motion of the tool can be generated. For example, the tool movement can be communicated relative to the patient reference frame by providing guidance such as "move posterior three millimeters" or the like. The magnitude of the required motion can also be indicated by an audio tone. For example, a large displacement can be indicated by a relatively high frequency tone, with a small displacement indicated by a relatively low frequency tone.

The invention has been described in relation to its preferred embodiment. Of course, modifications and alterations will occur to other upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for guiding the movement of a surgical toot in relation to the anatomy of a patient, the apparatus comprising:
   a surgical tool;
   a display remote from the tool for displaying a diagnostic image of the anatomy;
   a means for superimposing at least one of a proposed target and a proposed trajectory indicative of a desired position of the tool on the display;
   means for determining an actual position of the tool;
   means for determining a difference between the actual position of the tool and the desired position of the tool; and,
   indicating means different from the remote display and mounted on the tool for indicating to a human the difference between the actual and desired positions of the tool, the indicating means having an indicator reference frame different from the remote display frame of reference, the difference being indicated with respect to the indicator reference frame.

2. The apparatus of claim 1 wherein the indicating means comprises at least one indicator.

3. The apparatus of claim 1 wherein the means for deter the actual position of the tool comprises one of an infrared localizer and an articulated arm.

4. The apparatus of claim 1 wherein the actual and desired positions include at least one of a location, trajectory, depth, and rotation of the tool.

5. The apparatus of claim 1 wherein the indicating means comprises a position indicator and a mode indicator.

6. An apparatus for guiding the movement of a surgical tool in relation to the anatomy of a patient, the apparatus comprising:
   a surgical tool, wherein the surgical tool includes a pointing axis;
   a position determining means for determining an actual position and orientation of the pointing axis the surgical tool;
   a difference determining means for determining a difference between the actual position and orientation of the pointing axis of the surgical tool and a desired position and orientation of the pointing axis of the surgical tool;
   at least two electronic indicators mounted to the surgical tool in a plane substantially orthogonal to the pointing axis, the indicators being connected with the difference determining means to indicate the determined difference between the actual and desired position and orientation of the pointing axis, in a frame of reference of the surgical tool; and
   a display remote from the electronic indicators which displays a diagnostic image with the actual position and orientation of the pointing axis of the surgical tool and the desired position and orientation of the pointing axis of the surgical tool superimposed thereon.

7. The apparatus of claim 6, further including at least two pairs of electronic indicators.

8. An apparatus for use with an image guided surgery system, the apparatus comprising:
   a surgical tool;
   first and second display members associated with the tool and arranged along a first line and third and fourth display members associated with the tool and arranged along a second line, the first and second lines being perpendicular, the display members providing to a human operator an indication of a direction in which the tool should be moved to reach a desired position;
a mechanism for determining an actual position of the surgical tool;
a processor programmed to update the tool position, to control the first, second, third, and fourth display members, as the tool moves, to indicate deviations from a planned trajectory in a frame of reference of the display members.

9. A method for guiding the movement of a surgical tool with respect to the anatomy of a patient having a patient reference fame, the method comprising the steps of:
determining a desired position of the tool based on an image of the anatomy of a patient, the image having an image reference frame;
correlating the image and patient reference frames;
determining an actual position of the tool;
determining a direction in which the tool must be moved to reach the desired position;
determining an actual position of a human readable position display disposed remote from the tool having a display reference frame; and
utilizing the human readable position display to indicate the direction in which the tool must be moved to reach the desired position, said indication being provided in relation to the display reference fame.

10. The method of claim 9 wherein the human readable position display includes a plurality of light emitting diodes.

11. A method for guiding the movement of a surgical tool with respect to the anatomy of a patient having a patient reference frame, the method comprising the steps of:
displaying an image of the anatomy of the patient on a display disposed remote from the surgical tool;
determining a desired position of a tip of the tool based on the displayed image;
electronically determining a direction the tool must be moved for the tip to reach a desired position;
determining an actual position of the tip of the tool;
superimposing a representation of the tip of the tool on the image of the anatomy displayed on the display;
utilizing a position indicator mounted to the tool to indicate to a human the magnitude of the distance the tool must be moved for the tip to reach the desired position, said position indicator having an indicator reference frame, said indication being provided in relation to the indicator reference frame.

12. The method of claim 11, wherein said indication is provided by varying one of blink rate and color of an indicator visible to a user.

13. An apparatus comprising:
a surgical tool;
direction indicators attached to the tool for rotation therewith;
a mechanism for locating an actual location and orientation of a distal end of the tool with its attached direction indicators;
a mechanism for causing the direction indicators attached to the tool to indicate to a human a direction in a frame of reference of the tool in which the tool should be moved for the distal end to travel on a desired trajectory to a desired position; and,
a display which displays at least the actual location of the distal end and the desired position in a fixed frame of reference such that an orientation of the display remains fixed as the tool moves and rotates.

14. The apparatus of claim 13, wherein the direction indicators comprise a plurality of indicators disposed at angular intervals surrounding a central point.

15. The apparatus of claim 13, wherein the display includes a plurality of light emitting elements attached to the tool demarcating at least two different axes such that illumination of the light emitting elements is indicative of the direction in which the tool should be translated.

16. An apparatus comprising:
a tool for use in connection with surgery,
a first display remote from the tool which displays an anatomical image including target anatomy and a desired trajectory to be followed while moving the tool to the target anatomy;
a mechanism for locating an actual position of the tool relative to the target anatomy as the tool is moved toward the target anatomy;
a second display mounted on the tool for indicating differences between the actual position of the tool and the desired trajectory, wherein said differences are indicated with respect to the tool; and
a mechanism for causing the second display to indicate to a human a direction in a frame of reference of the second display which the tool should be moved to reach the target anatomy.

17. A method for guiding the movement of a surgical tool, said method comprising:
tracking a surgical tool with reference to a patient's anatomy;
determining a direction in which the surgical tool should be moved from an actual position for a distal end to reach a desired position with respect to the patient, the desired position being indicated with reference to a diagnostic image of the patient displayed on a display remote from the surgical tool in a frame of reference which is fixed relative to a frame of reference of the patient's anatomy; and
activating a display on the surgical tool adjacent a handle end to indicate the direction in a frame of reference of the tool in which a handle end of the tool should be moved to move a distal end of the tool from the determined actual position to reach the desired position, the tool frame of reference changing relative to the frame of reference of the diagnostic image and the patient's anatomy with movement of the tool.

18. An apparatus, comprising:
a hand-held surgical tool to which a position indicator is mounted;
a tool position tracker for tracking a position and orientation of the hand-held tool and the direction indicator with respect to a reference frame;
the direction indicator being configured to produce a visual indication of a direction in which a hand-held portion of the tool should be moved to reach a desired position based at least in part on the position and orientation of the tool as determined by the tool position tracker, the indicated direction being relative to a reference frame of the hand-held surgical tool which surgical tool frame of reference changes relative to a frame of reference of the patient as the surgical tool moves relative to the patient; and
a display remote from the tool and the direction indicator which displays a diagnostic anatomical image of the patient with a representation of the tool in its current position and orientation superimposed thereon.

* * * * *